United States Patent [19]

Cracauer et al.

[11] 4,405,320
[45] Sep. 20, 1983

[54] SEPTUM RETAINING MEANS FOR PERCUTANEOUS DEVICE

[75] Inventors: Raymond F. Cracauer, Minneapolis; Larry E. Fuller, Minnetonka; Felix J. Martinez, Plymouth; Louis C. Cosentino, Wayzata, all of Minn.

[73] Assignee: Renal Systems, Inc., Minneapolis, Minn.

[21] Appl. No.: 350,574

[22] Filed: Feb. 22, 1982

[51] Int. Cl.³ .............................................. A61M 5/00
[52] U.S. Cl. .................................... 604/175; 220/307
[58] Field of Search .................. 604/4, 8, 9, 175, 905; 220/307, DIG. 19; 128/1 R

[56] References Cited

U.S. PATENT DOCUMENTS

| | | | |
|---|---|---|---|
| 4,014,328 | 3/1977 | Cluff et al. | 604/175 X |
| 4,016,884 | 4/1977 | Kwan-Gett | 604/175 |
| 4,043,474 | 8/1977 | McCord | 220/307 X |
| 4,092,983 | 6/1978 | Slivenko | 604/175 |
| 4,269,237 | 5/1981 | Berger | 220/307 X |
| 4,350,157 | 9/1982 | Hoffa | 604/175 |

Primary Examiner—Richard J. Apley
Assistant Examiner—Michelle N. Lester
Attorney, Agent, or Firm—Everett Schroeder; Kenneth Siegfried; Robert O. Vidas

[57] ABSTRACT

Septum retaining means for an implantable tubular percutaneous device. The retaining means is a tubular stem insert having an integral pressure plate across an intermediate portion thereof. A modified septum fits into the insert below the pressure plate. Tabs extending outwardly from the upper edge of the insert cooperate with a grooved portion of a body exterior cavity in the T-stem to provide means for holding the insert in the T-stem cavity. Notches in the walls of the insert on either side of the tabs allow the wall portions containing the tabs to be flexed inwardly so as to permit the insert to be passed into and out of the T-stem. The insert is designed to permit a forceps or other crimping tool to obtain access to the tab containing insert wall portions for removal of the insert and septum.

15 Claims, 20 Drawing Figures

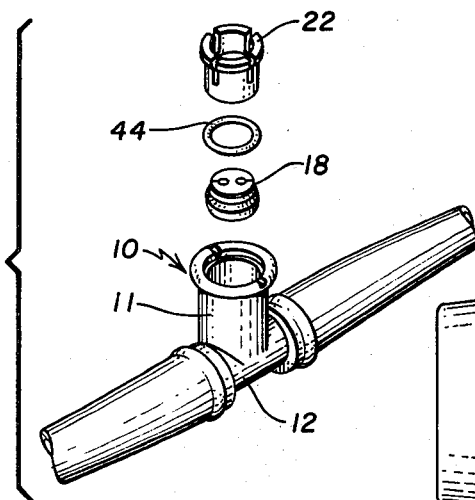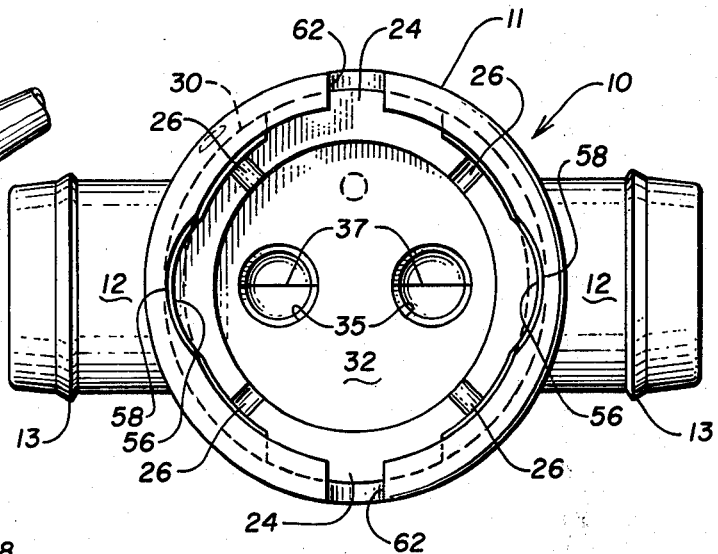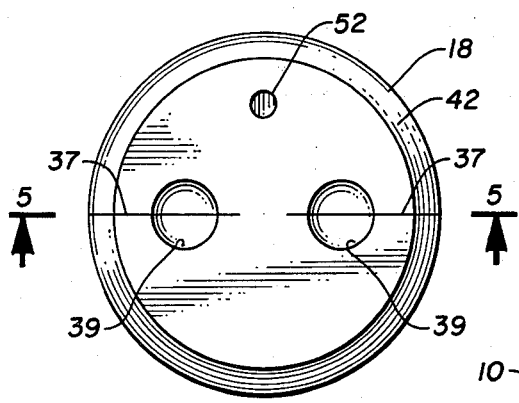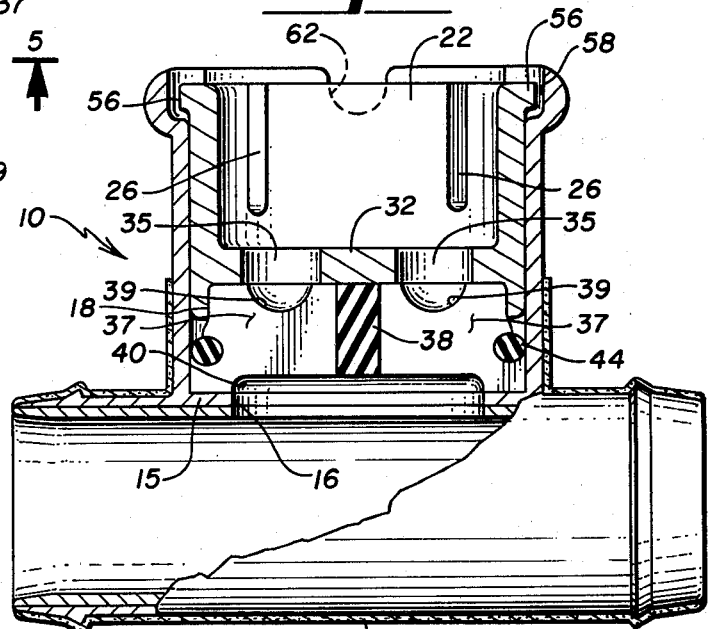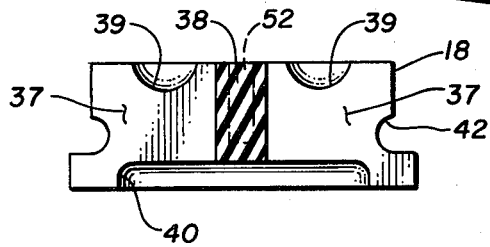

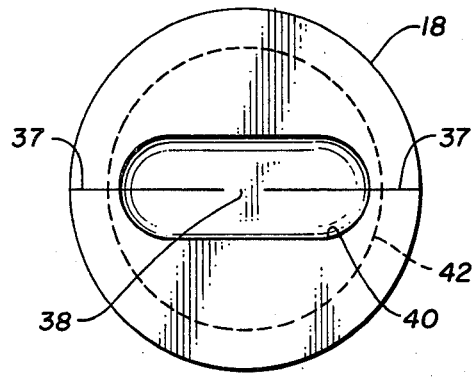
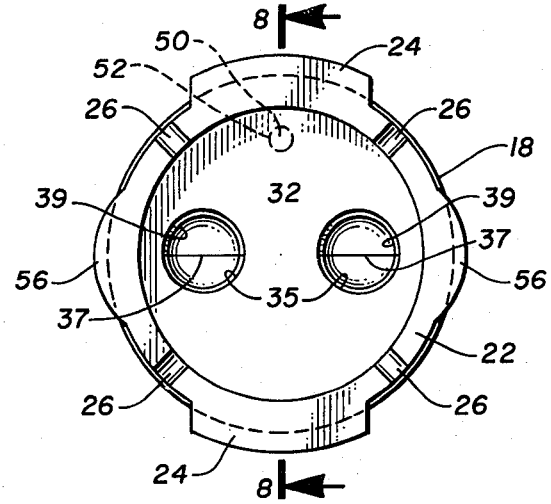
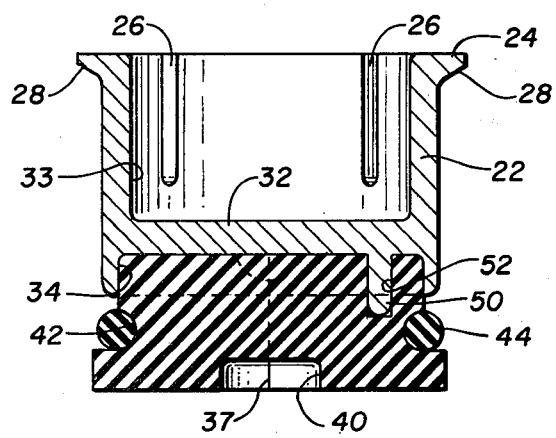
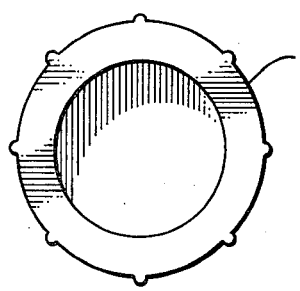
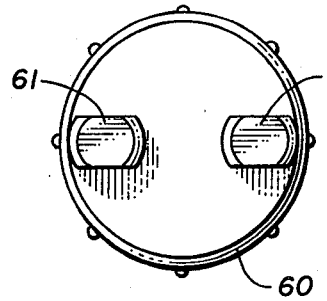
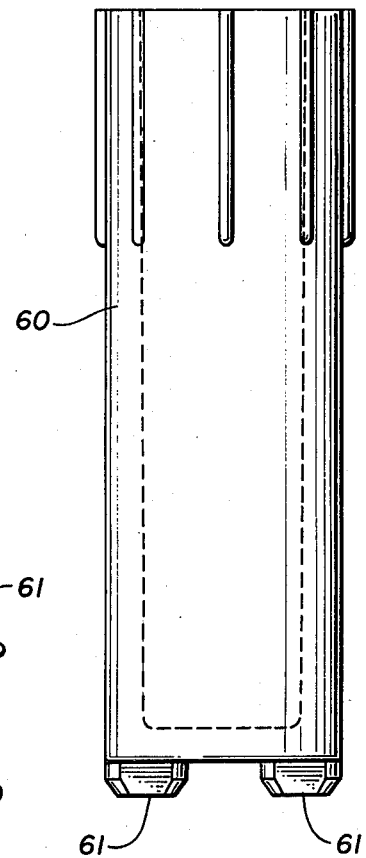

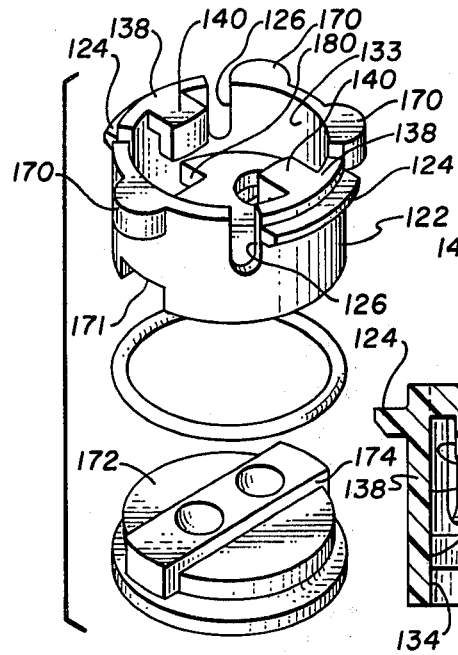
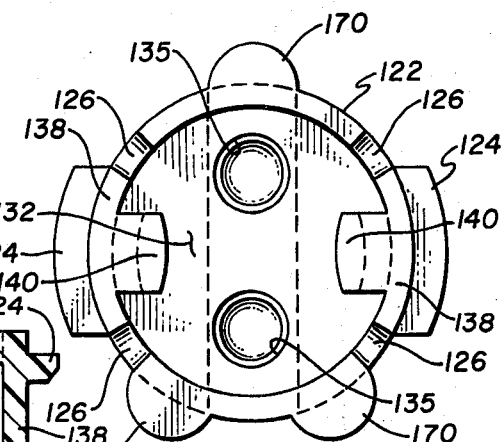
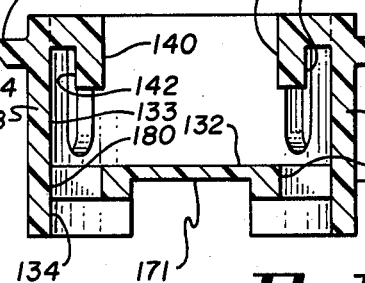
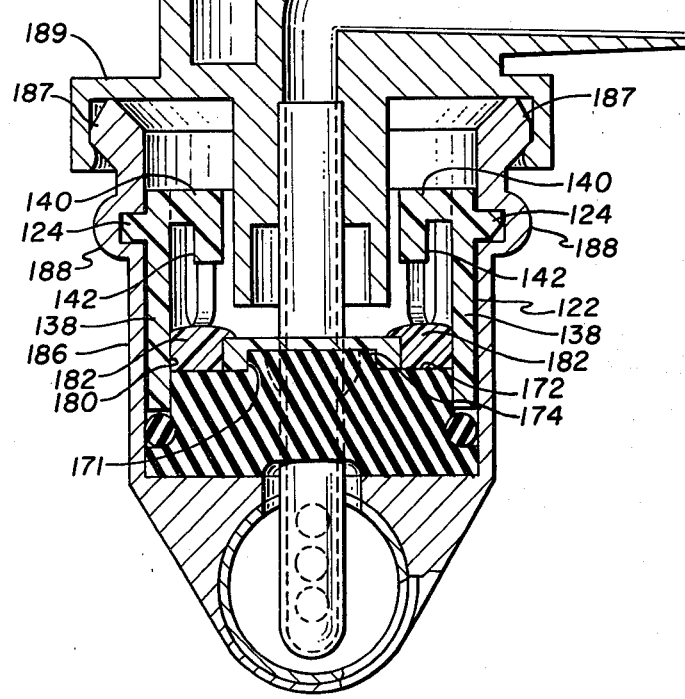
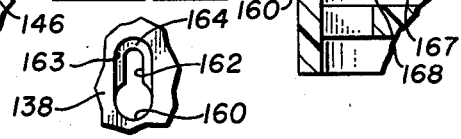
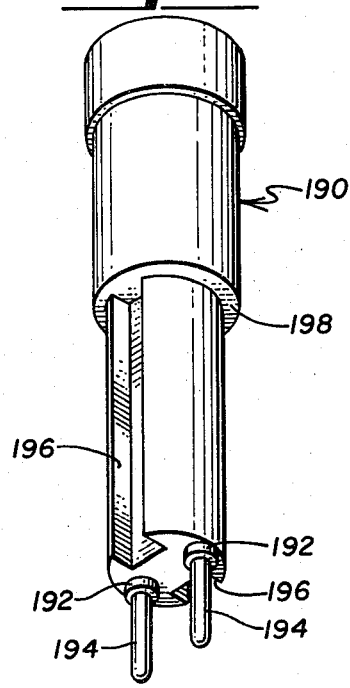

SEPTUM RETAINING MEANS FOR PERCUTANEOUS DEVICE

DESCRIPTION

BACKGROUND OF THE INVENTION

This invention relates to a means for holding a septum in a septum closed tubular percutaneous device and to special septum configurations therefor.

In co-pending application Ser. No. 261,709 filed May 8, 1981, as a Continuation of Ser. No. 138,579 filed Apr. 8, 1980, there is disclosed an implantable generally T-shaped percutaneous structure in which the stem of the T is constructed and arranged to cooperate with a needle structure that penetrates a septum seal means at the junction of the stem of the T with the balance of the T structure. The arms of the T may be connected to a blood vessel directly or via intermediate flexible tubes of a material such as expanded polytetrafluorethylene. The T-stem protrudes through the skin layer, thereby providing access to the circulatory system through the septum. By reason of the structure of the invention, the interior stemmed portion of the T can be rinsed clean and sterilized between each use without elaborate procedures, thus minimizing the likelihood of infection as a result of access to the circulatory system.

In co-pending application, Ser. No. 209,058, filed Nov. 21, 1980, there are described a number of improvements and accessories for such a tubular T-shaped blood access device. These improvements include a pre-slit septum having a circumferential side groove which carries an elastomeric O-ring for extended sealing life, an improved cooperating needle carrier structure, a septum assembly insertion tool and a variety of additional structure and accessories.

In co-pending application, Ser. No. 314,569, filed Oct. 26, 1981, as a continuation-in-part of application Ser. No. 261,709, there are described similar tubular, septum closed, percutaneous devices for other applications, such as peritoneal dialysis and chemotherapy.

The disclosures of applications Ser. Nos. 261,709, 209,058 and 314,569 are incorporated herein by reference.

The means for retaining the septum in the stem of the percutaneous devices of the aforementioned applications, Ser. Nos. 261,709, 209,058 and 314,569, is a pressure plate defining a pair of needle holes therethrough which is in turn held in place by a retaining ring fitted into a groove in the T-stem. This structure can be very cumbersome during removal and replacement of the septum. Septum replacement in such a structure entails sequential removal of the retaining ring, the pressure plate and the septum followed by replacement of new piece parts. While steps may be taken to reduce blood flow during replacement, substantial blood loss can occur even when a specialized septum loading tool as described in application Ser. No. 209,058 is used to simultaneously insert the new septum, pressure plate and retaining ring.

BRIEF DESCRIPTION OF THE INVENTION

The present invention relates to alternative septum retaining means for implantable tubular percutaneous devices. The retaining means comprises a tubular stem insert having an integral pressure plate member across an intermediate portion thereof and defining at least one opening therethrough. The insert has a pair of outwardly extending tabs which lock into a grooved portion of the stem near the top of the stem. The upper portion of a modified septum fits snugly into the insert below the integral pressure plate so that the septum and insert may be inserted and removed as a single unit. Elongated grooves in the body of the insert above the shelf portion permit the upper insert walls to flex, thereby permitting the insert to be snapped into place in the T-stem retaining grooves. In one embodiment, notches in the T-stem permit access to the insert retaining tabs by a crimping tool such as a forceps so that the insert and septum may be rapidly removed. In the preferred embodiments, the insert is provided with a pair of lugs or slots which may be engaged by a forceps tool to crimp the retaining tab portions inward for removal of the insert.

The septum retaining means of the present invention results in a substantial reduction in the level of technical skill necessary to accomplish a rapid septum change. Instead of fumbling with sequential removal of a small retaining ring, a pressure plate and a septum deep within the stem cavity, the present invention now permits septum removal to be accomplished with a forceps or similar tool applied to readily visible and easily accessible points at the top of the stem.

Insertion of the replacement septum is also accomplished as a one-step operation, involving simply pushing a preassembled septum and insert combination into the stem cavity with an insertion rod.

BRIEF DESCRIPTION OF THE DRAWINGS

FIG. 1 is an exploded pictorial view of an implantable T-shaped blood access device including the insert and septum of the present invention.

FIG. 2 is a top plan view of the implantable T-shaped assembly with the inventive insert and septum included therein;

FIG. 3 is a side view of the implantable blood access device, including an optional exterior coating of porous titanium, with parts cut away showing the insert and septum in place within the device stem;

FIG. 4 is a plan view of the top side of the septum of the present disclosure;

FIG. 5 is a side section view along lines 5—5 of FIG. 4;

FIG. 6 is a plan view of the bottom interior facing side of the septum of the present disclosure;

FIG. 7 is a top plan view of the insert with septum prior to insertion into the blood access device;

FIG. 8 is a side sectional view of the insert and septum taken along the lines 8—8 of FIG. 7;

FIG. 9 is a side elevational view of an insertion rod for use with the device of FIGS. 1 through 8;

FIG. 10 is a top plan view of the insertion rod;

FIG. 11 is a bottom plan view of the insertion rod;

FIG. 12 is an exploded view of a preferred insert and septum assembly;

FIG. 13 is a top plan view of the preferred insert and septum assembly;

FIG. 14 is an end elevational view of a preferred insert assembly in place within a blood access device with a cooperating needle assembly inserted therethrough;

FIG. 15 is a cut-away view of the preferred insert with part of a removal tool shown in association therewith;

FIGS. 16, 17 and 18 show cut away portions of the insert assembly with alternative removal means and removal tools associated therewith;

FIG. 19 is an external side elevational view of a keyhole removal means element as shown in FIG. 18; and FIG. 20 is a pictorial view of a modified insertion tool for the preferred insert of FIGS. 12-15.

DETAILED DESCRIPTION OF THE INVENTION

Referring to the drawings, there will be seen in FIG. 1 an implantable blood access device which includes a T-shaped unitary tubular body generally designated 10 having a stem portion 11 and a straight body tube portion 12. Body 10 is formed as a unitary body from a biologically compatible material such as titanium. The body 10 may be coated with pyrolytic carbon to enhance biocompatibility. To aid in accomplishing tissue in growth onto the portion of the stem below the skin, the surfaces of body 10 below the skin may have a matte or porous finish. Alternatively, the surfaces below the skin may be coated with a porous material such as polyethyleneterephthalate to promote tissue in growth. The embodiment of body 10 shown in FIG. 3 includes optional porous titanium layer 14 on its exterior below the skin surfaces.

The implanted device may be placed directly in a blood vessel. In such a case, the blood vessel would be slit longitudinally for sufficient distance for the device 10 to be inserted and the vessel drawn around the device over ridges 13 on tubular portion 12 and sutured into place. Alternatively, polymeric tubing, preferably tapered tubing, may be used as an intermediary connection between the ends of tubular portion 12 and the blood vessel.

As can be seen in FIG. 3, body 10 is formed with an internal extension 15 which substantially provides a separation of the internal cavity of T-stem 11 from the internal chamber of portion 12 except for the opening 16. Member 15 provides a support surface of an elastomeric septum member 18 through which a needle or needle pair may gain access to the blood stream.

The septum is held in place under sealing pressure by a novel insert member 22 which serves both as retaining means and as a pressure plate for the septum.

Insert 22 is a generally tubular member which fits closely into the interior cavity of stem 11. The upper edge of the insert is provided with a pair of outwardly extending tabs 24 on opposite sides thereof. The walls of insert 22 are provided with elongated notches 26 therethrough on both sides of tabs 24. Notches 26 permit the insert wall portion containing tabs 24 to flex inwardly when inward pressure is applied to the tabs. The undersurfaces 28 of tabs 24 are tapered so that when the insert is placed into the interior cavity of stem 11 and downward pressure applied to the insert, the insert wall portions containing tabs 24 will flex inwardly permitting the tabs to pass below the upper lip of stem 11. The tabs snap into circumferential groove 30 of the interior surface of stem 11.

The lower portion of the insert body is provided with an integral shelf member or pressure plate 32 which extends across the interior cavity of insert 22, dividing the interior cavity of insert 22 into an upper chamber 33 and a lower chamber 34. Plate 32 defines a pair of holes 35 therethrough for which a needle pair may pass into the blood stream through the septum. As shown in FIG. 8, the upper portion of septum 18 fits snugly into the lower insert chamber 34.

As shown in FIGS. 4, 5 and 6, septum 18 is a modified version of the septum described in co-pending application Ser. No. 209,058. The septum which is preferably made of a silicone elastomer, has a generally circular shape with a pair of slits 37 extending from opposite sides toward the center thereof. An unslit central portion 38 holds the septum together. A pair of semispherical depressions 39 in the top of the septum centered on the slits and spaced correspondingly with holes 35 in plate 32 provide entry points for a needle or other cannulae. The bottom of the septum is provided with an elongated oval depression 40 which provides further relief for the septum when the needles are inserted therethrough. Circumferential groove 42 in the sides of the septum carries an elastomeric band or O-ring 44 whose interior diameter at rest is less than the diameter of groove 42. Ring 44 provides inwardly directed circumferential force to hold the septum together and to maintain the slits in sealed relationship against each other or around an inserted needle. Unlike the septum or application Ser. No. 209,058, however, the septum portions above and below groove 42, respectively, do not have the same dimensions. Whereas, the upper portion of septum 18 is sized to fit snugly within the cavity 34 of the insert member 22, the lower portion of septum 18 in the rest state is slightly larger than that of insert member 22. The lower portion of septum 18 conforms generally with the interior configuration of the lower stem cavity so that, when the septum is inserted in the cavity of stem 11 and held there under pressure applied by plate 32 of insert member 22, the lower portion of septum 18 seals against the interior wall of stem 11 and against supporting surface 15.

Since the septum of the present invention is preferably circular, some means to assure proper alignment of septum slits 37 with insert holes 35 is desirable. This may be done by providing the insert with an off-center pin 50 which projects into insert chamber 34 from plate 32. A corresponding hole 52 in septum 18 which extends partway through the septum from the top thereof, accommodates pin 50, aligning the septum slits with the insert holes.

To assure that the needle slits are aligned with the longitudinal access of the body 10, the upper edge of insert 22 may be provided with semi-circular outwardly extending lugs 56 which fit into correspondingly shaped depressions 58 in the upper interior wall of stem 11.

Insertion of the septum and insert is a single step operation. The septum is placed in lower chamber 34 of insert 22 as shown in FIG. 8. A rod-like insertion tool such as member 60 which is shown in FIGS. 9-11 is placed in the upper chamber 33 of the insert member. The insert and septum assembly is placed in the cavity of stem 11 with lugs 56 in alignment with depressions 58. Body 10 is held by means of the portion of stem 11 extending above the skin surface, while downward pressure is exerted on plate 32 by means of rod 60. Rod 60 has two lower protrusions 61 which fit into holes 35 of plate 32 to maintain the rod in the center of the insert. Rod 60 may also be provided with two short, round ended pins, protruding downward from protrusions 61 which extend into the septum slits 37 to engage and hold the insert/septum assembly during insertion. The diameter of rod 60 is less than the interior diameter of chamber 33 permitting the portions of the insert wall containing tabs 24 to be flexed inwardly. The downward pressure on rod 60 causes the insert wall portions containing tabs 24 to flex inward and allows the septum and insert assembly to be pushed into the stem cavity until tabs 24 engage stem groove 30. The depth of stem groove 30 is set so as to maintain the septum in the stem cavity under slight compression to assure proper sealing.

For convenient removal of the septum and insert, a pair of grooves 62 are provided in the upper lip of stem 11. These grooves are aligned with a central portion of tabs 24 when the insert and septum are in place within the stem cavity. The grooves extend below the upper edge of the insert member so that access to tabs 24 may be achieved by a crimping tool such as a forceps. To remove the insert and septum, the tabs 24 are squeezed inwardly and the insert pulled out of the stem cavity by means of such a tool. Because the upper portion of septum 18 is held snugly within cavity 34 of the insert member, the septum comes out with the insert in a single operation.

FIGS. 12–20 show details of preferred embodiments of the present invention. The preferred inserts are designed so that they may be conveniently removed from the stem of a percutaneous device which does not include the notches 62, shown in FIGS. 2 and 3, in the upper lip of the stem. The preferred inserts also utilize improved alignment means for orienting the septum in the insert and for aligning the insert in the percutaneous device stem.

The preferred insert structure is designated by the numeral 122. The device includes a pair of diametrically opposed outwardly extending locking tabs 124 near the upper edge thereof and elongated slots 126 through the walls of the upper chamber. As with the embodiment of FIGS. 1–8, the upper chamber 133 is divided from the lower chamber 134 by an integral pressure plate member 132, including a pair of needle openings 135 therethrough.

Slots 126 define a portion 138 of the walls of the upper chamber from which locking tabs 124 extend outwardly. Wall portions 138 also include a pair of removal tabs 140, which extend inwardly to the cavity of the upper chamber 133. These removal tabs 140 include grooves 142 on the underside thereof which may be engaged by a forceps which includes hook-shaped ends 144 as shown in FIG. 15. To remove the insert, the forceps is inserted into the cavity of chamber 133 and the ends 144 thereof brought into engagement with grooves 142 of the removal tabs. By squeezing the forceps together, the insert wall portions 138 will be flexed inwardly, disengaging the locking tabs 124 from the groove in the side wall of the percutaneous device, thereby permitting removal of the insert and septum assembly.

Alternative removal means are shown in FIGS. 16–19. The alternative of FIG. 16 includes an inwardly extending removal tab 145. Tabs 145, rather than having a groove in the underside thereof, merely have a hole 146 extending through the tab. The ends of a forceps 147 are passed through the hole and squeezed together to disengage tabs 124 from the percutaneous device stem. The forceps are preferably provided with an enlarged disk-like tip portion 148 which can engage the underside of tab 145 during the removal procedure so that the insert and septum assembly may be easily lifted from the stem of the percutaneous device.

FIG. 17 shows another alternative removal means structure. In FIG. 17, rather than utilizing inwardly extending tabs, the side wall portions 138 above tab member 124 include a hole 150 therethrough which is enlarged on the outside of the wall, leaving a thin inner wall portion 152 which may be engaged by hooked forceps ends 154 permitting the wall portion 138 to be flexed inwardly and the insert lifted from the stem of the percutaneous device.

FIGS. 18 and 19 show a keyhole slot removal means similar to that of FIG. 17. Wall portions 138 include a hole 160 therethrough with a narrow slot 162 extending upwardly. A wider slot, the width of hole 160, extends upwardly, concentric with slot 162. Slot 163 extends only part way through wall portion 138 from the outside thereof. This leaves a narrow shoulder portion 164 of wall 138 which may be engaged by a modified forceps tool. The modified forceps tool includes L-shaped ends 167 having an enlarged disk end portion 168 which may pass through hole 160 and engage the thin slot wall portion 164, so as to permit wall 138 to be flexed inwardly and the insert to be lifted from the percutaneous device.

Structures embodying one of the removal means shown in FIGS. 15–19 are preferred to that of FIGS. 1–8 because it is not necessary to provide the stem of the percutaneous device with slots 62 in the upper lip thereof. This, in turn, permits better sealing of snap-type cap structures which are typically placed on the device when not in use to protect the interior of the stem from contamination and to retain a sterilizing fluid within the stem cavity.

The inventive device may also be provided with three alignment lugs 170 which fit into corresponding depressions in the upper interior wall of stem 11. The use of a three-lug alignment structure permits additional latitude in manufacturing tolerances of the insert while achieving the same alignment accuracy. In blood access applications where careful alignment of the needle openings with respect to the blood flow through the arms of the device is desirable, it is preferred that the alignment lugs 56 or 170 touch the interior side walls of the stem cavity of the blood access device with slight compression. This positive contact between the alignment lugs and the interior wall of the stem cavity provides an additional incremental improvement in the alignment of the insert within the stem cavity.

To accurately align the septum in the inserts so that the septum slits are always accurately oriented with respect to holes 135 and integral pressure plate 132, the insert member 122 preferably includes an elongated slot 171 in the bottom of pressure plate 132 and extending through the side walls of the lower chamber of the insert, as is shown in FIG. 15. The upper portion of the septum 172 includes an elongated ridge 174, shown in FIGS. 12 and 14, which fits into slot 171 so as to properly orient the septum in the insert.

In the preferred structure, the septum will be adhesively bonded to the insert so as to assure that orientation is maintained during insertion and to assure that the septum and insert come out of the stem of the percutaneous device as a single unit. A medical grade silicone adhesive may typically be used to bond the upper surface of the septum 172 to the insert. To facilitate such adhesive bonding, pressure plate 132 may be provided with holes 180 therethrough in addition to the needle holes 135. As shown in FIG. 14, beads 182 of silicone adhesive may be placed in holes 180 so as to contact the septum 172 and overlap the upper surface of pressure plate 132. The septum becomes securely bonded to the insert member 122 when the adhesive beads 182 set up.

As indicated in FIG. 14, the stem 186 of the percutaneous device into which the insert/septum assembly of the present invention is placed preferably includes two excutaneous circumferential ridges 187 and 188, respectively. Ridge 187 forms a lip on the top of the stem over which a needle or cannulae assembly 189 may be snapped. When the needle assembly is removed, a cap member, not shown, may be snapped over lip ridge 187. The lower ridge 188 provides a gripping surface around which a forceps, such as disclosed in co-pending application Ser. No. 209,058, may be clamped to hold the device securely during insertion and removal of the insert/septum assembly.

The insert structures of the present invention may be manufactured of a body compatible metal. Alternatively, they may be manufactured by injection molding of an appropriate plastic, such as polycarbonate or polysulfone. A reinforcement, such as glass, mineral or carbon, may be used in the plastic composition to improve its flexural and hardness characteristics.

The preferred insert of FIGS. 12-15 requires a slightly modified insertion tool from that of FIGS. 9-11. The modified tool is shown in FIG. 20 and generally designated by the numeral 190. The tool of FIG. 20 includes protrusion 192 on the lower surface thereof for engaging the tool in holes 35 so as to properly center the tool in the upper chamber of the stem. Pins 194 extend downwardly from protrusions 192 for engagement with the septum slits to hold the septum/insert assembly during the insertion step. The modified insertion tool includes slots 196 in the sides thereof which permit the tool to be passed between removal lugs 140. The insertion member 190 may also be provided with an enlarged upper section for convenient manipulation. Shoulder 198 between the upper and lower sections of the insertion tool is spaced so that the shoulder contacts the upper lip of the stem of the percutaneous device when insertion of the insert/septum assembly is complete.

It will be readily seen that various modifications from the specific structures disclosed herein may be made without departing from the present invention, the scope of which is defined by the following claims.

What is claimed is:

1. In a percutaneous device having a generally tubular body with the body exterior tubular portion including communication with a body interior portion, said device including a septum closure in the tubular portion and a removable retaining means for retaining said septum within the tubular cavity of said device, wherein the improvement resides in the retaining means, a septum closure in the stem portion, said improved retaining means comprising a tubular septum retaining insert, the exterior configuration of which closely conforms to the configuration of the stem cavity, the insert including:

an integral pressure plate member located at an intermediate region between the top and the bottom of said insert so as to define an upper insert chamber above the pressure plate and a lower insert chamber below the pressure plate, said pressure plate having at least one cannula hole therethrough; and, at least one locking tab member projecting outwardly from near the upper edge of said insert, said locking tab sized to fit within a retaining groove within the stem cavity, each said locking tab having on either side thereof an elongated notch extending downwardly through the insert wall whereby the insert wall portion carrying the tab may be flexed inwardly and the insert may be passed into and out of the stem cavity.

2. The device as in claim 1 wherein the retaining means has two said insert locking tab members diametrically opposed.

3. The device as in claim 1 wherein the lower surface of said insert locking tab member is tapered so that the minimum tab thickness is at the outer edge thereof.

4. The device as in claim 1 wherein the retaining means further includes alignment means for orienting the insert within the tubular cavity.

5. The device as in claim 1 wherein said insert has at least one alignment pin extending downwardly into said lower insert chamber from said integral pressure plate.

6. The device as in claim 1 wherein said insert includes a septum alignment groove extending along the bottom surface of said integral pressure plate.

7. The device as in claim 1, wherein the retaining means includes insert removal means on the locking tab carrying portions of sidewalls thereof, whereby said locking tab carrying portions of the sidewalls may be engaged by a crimping tool and flexed inwardly for disengaging the locking tabs from the tubular cavity of the percutaneous device.

8. The device as in claim 1 wherein the septum has a top surface, a bottom surface and a stepped circumferential side surface, the upper portion of said side surface conforming to the configuration of said lower insert chamber and the lower portion of said side surface conforming to the configuration of the tubular cavity at the bottom thereof.

9. The device as in claim 8 wherein the septum further comprises a circumferential groove in the side surface between the upper and lower portions thereof, an elastomeric ring within the groove, said ring having an interior diameter at rest less than that of said groove, and at least one elongated slit through the septum from the top surface to the bottom surface whereby a needle or other cannulae may be passed through the septum.

10. The device as in claim 8 wherein said insert and septum held within the implantable device by means of a groove in the interior wall of said body exterior tubular portion into which said tab members are fitted.

11. The device as in claim 10 wherein said insert has two said tab members diametrically opposed, said tabs are tapered so that the minimum tab thickness is at the outer edge thereof and said implantable device further has two notches through the upper edge of the tubular, aligned with said tab members, said notches providing means for a crimping tool to obtain access to said tabs so that the tabs may be squeezed inwardly to permit removal of said insert and septum from the tubular cavity.

12. The device as in claim 10 wherein said insert includes removal means on the locking tab carrying portions of the sidewalls thereof, whereby said locking tab carrying portions of the sidewalls may be engaged by a crimping tool and flexed inwardly for disengaging the locking tabs from said body exterior tubular portion groove.

13. The device as in claim 10 or 12 wherein said implantable device body exterior tubular portion includes a pair of circumferential ridges on the exterior upper portion thereof, the first said ridge forming a lip on the upper edge of the body exterior tubular portion and providing a surface over which a cap or cannulae assembly may be snapped and the second said ridge located below said first ridge and providing an excutaneous gripping surface on the implantable device.

14. The device as in claim 13 in combination with said cannulae assembly, the cannulae assembly including means for engaging said body exterior tubular portion lip to hold the cannulae assembly in place on the implantable device.

15. The device as in claim 8 in combination with means for inserting said retaining means and septum into the implantable device, said inserting means comprising a rod-like member including at one end thereof at least one alignment protrusion whereby the rod may be centered in the upper insert chamber when said protrusion is placed in an integral pressure plate cannulae hole.

* * * * *

UNITED STATES PATENT AND TRADEMARK OFFICE
CERTIFICATE OF CORRECTION

PATENT NO. : 4,405,320

DATED : September 20, 1983

INVENTOR(S) : Raymond F. Cracauer et al

It is certified that error appears in the above-identified patent and that said Letters Patent are hereby corrected as shown below:

Claim 11, line 5, delete "tubular" and insert - body exterior tubular portion -

Signed and Sealed this

Twenty-second Day of November 1983

[SEAL]

Attest:

GERALD J. MOSSINGHOFF

Attesting Officer

Commissioner of Patents and Trademarks